US008382663B2

(12) United States Patent
Taylor et al.

(10) Patent No.: US 8,382,663 B2
(45) Date of Patent: Feb. 26, 2013

(54) SURGICAL DEVICES, SYSTEMS AND METHODS THEREOF HAVING GEL MATERIAL, GEL COATINGS, OR GEL LUBRICANTS

(75) Inventors: Scott V. Taylor, Mission Viejo, CA (US); Kimball B. McGinley, Laguna Niguel, CA (US); John Stout, Irvine, CA (US); Arkadiusz A. Strokosz, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1279 days.

(21) Appl. No.: 11/549,872

(22) Filed: Oct. 16, 2006

(65) Prior Publication Data

US 2007/0116854 A1    May 24, 2007

Related U.S. Application Data

(60) Provisional application No. 60/726,822, filed on Oct. 14, 2005.

(51) Int. Cl.
*A61B 1/00*  (2006.01)
(52) U.S. Cl. ...................................... 600/184
(58) Field of Classification Search .............. 600/184; 604/164.02, 167.01, 167.02, 167.03, 167.04, 604/167.06; 606/167, 170, 185, 190; 524/261, 524/269, 505, 506
See application file for complete search history.

(56) References Cited

U.S. PATENT DOCUMENTS

| | | | |
|---|---|---|---|
| 3,971,385 A * | 7/1976 | Corbett .................... | 128/207.15 |
| 4,386,179 A * | 5/1983 | Sterling .................... | 524/269 |
| 5,041,100 A | 8/1991 | Rowland et al. | |
| 5,098,379 A * | 3/1992 | Conway et al. ............ | 604/523 |
| 5,104,389 A * | 4/1992 | Deem et al. ................ | 604/264 |
| 5,186,972 A | 2/1993 | Williams et al. | |
| 5,197,955 A | 3/1993 | Stephens et al. | |
| 5,207,656 A | 5/1993 | Kranys | |
| 5,290,585 A | 3/1994 | Elton | |
| 5,350,364 A | 9/1994 | Stephens et al. | |
| 5,480,410 A | 1/1996 | Cuschieri et al. | |
| 5,662,615 A | 9/1997 | Blake, III | |
| 5,884,639 A * | 3/1999 | Chen ......................... | 132/321 |
| 5,922,351 A | 7/1999 | Daher | |
| 6,221,061 B1 | 4/2001 | Engelson et al. | |
| 6,764,107 B1 * | 7/2004 | Obahi et al. ............... | 285/322 |
| 6,939,296 B2 | 9/2005 | Ewers et al. | |

(Continued)

FOREIGN PATENT DOCUMENTS

EP    1 582 158 A    10/2005
WO    WO 02/34108    *    5/2002

(Continued)

OTHER PUBLICATIONS

International Bureau of WIPO, International Preliminary Report on Patentability for International Application No. PCT/US2006/060013, mailed Apr. 24, 2008.

(Continued)

*Primary Examiner* — Ryan Severson
*Assistant Examiner* — Jonathan W Miles
(74) *Attorney, Agent, or Firm* — Rimas T. Lukas; Pui Tong Ho; Cynthia A. Bonner

(57) ABSTRACT

Gel materials, and surgical devices containing gel materials, having reduced tackiness while retaining low durometer, high tear strength, high elongation, high compliance, and resistance to compression are described.

30 Claims, 5 Drawing Sheets

U.S. PATENT DOCUMENTS

| | | |
|---|---|---|
| 7,008,979 B2 * | 3/2006 | Schottman et al. ............ 523/334 |
| 7,563,250 B2 * | 7/2009 | Wenchell .................. 604/167.01 |
| 2004/0015185 A1 | 1/2004 | Ewers et al. |
| 2004/0093018 A1 | 5/2004 | Johnson et al. |
| 2004/0106942 A1 | 6/2004 | Taylor et al. |
| 2004/0167559 A1 | 8/2004 | Taylor et al. |
| 2005/0033246 A1 | 2/2005 | Ahlberg et al. |
| 2005/0059865 A1 | 3/2005 | Kahle et al. |
| 2006/0030755 A1 | 2/2006 | Ewers et al. |
| 2006/0047284 A1 | 3/2006 | Gresham |

FOREIGN PATENT DOCUMENTS

| | | |
|---|---|---|
| WO | WO 03/032819 A | 4/2003 |

OTHER PUBLICATIONS

International Search Report and Written Opinion for International Application No. PCT/US2006/060013, mailed Nov. 19, 2007.

\* cited by examiner

US 8,382,663 B2

SURGICAL DEVICES, SYSTEMS AND METHODS THEREOF HAVING GEL MATERIAL, GEL COATINGS, OR GEL LUBRICANTS

CROSS REFERENCE TO RELATED APPLICATIONS

This application claims the benefit of U.S. Provisional Application No. 60/726,822 filed Oct. 14, 2005, the disclosure of which is hereby incorporated by reference as if set forth in full herein.

BACKGROUND

Surgical devices having a gel component have been previously described. Examples include gel rollers in trocar seal housings, gel-containing caps in hand access devices and various other types of devices used in surgical and/or medical procedures. Examples of such devices are described in U.S. patent application Ser. No. 10/913,565, filed Aug. 5, 2004, U.S. patent application Ser. No. 10/776,387, filed Feb. 10, 2004, and U.S. patent application Ser. No. 10/381,220, filed Mar. 20, 2003; see also, U.S. Provisional Patent Application No. 60/241,958, filed Oct. 19, 2000, U.S. Provisional Patent Application No. 60/492,949, filed Aug. 6, 2003, and U.S. Provisional Patent Application No. 60/312,683, filed Aug. 14, 2001, the entire disclosures of which are hereby incorporated by reference as if set full herein.

Typically, the gel material performs a sealing function, conforming around the exterior of medical instruments inserted into a patient's body cavity through the gel (in the case of hand access devices, for example) or between gel rollers (in the case of trocar seals, for example) to prevent escape of insufflation gases or body fluids. Thus, it is important that the gel material be compliant enough to permit passage of medical instruments (or the surgeon's hand, in the case of hand access devices), but also resist compression and tearing.

One example of a gel material, suitable for use in some surgical devices, is a KP-12 copolymer gel, where the copolymer component of the gel comprises an SEBS (styrene ethylene butylene styrene) copolymer. The KP-12 gel material comprises a mixture of a KRATON® SEBS copolymer, PENRECO® DRAKEOL® mineral oil, a colorant, and an antioxidant. Such examples are described in U.S. patent application Ser. No. 10/776,387, filed Feb. 10, 2004 and U.S. patent application Ser. No. 10/913,565, filed Aug. 5, 2004, and U.S. Provisional Patent Application No. 60/492,949, filed Aug. 6, 2003 and U.S. Provisional Patent Application No. 60/312,683, filed Aug. 14, 2001, the entire disclosures of which are hereby incorporated by reference as if set in full herein.

Ideally, gels used in surgical devices have low durometer, high tear strength, high elongation, high compliance, and a resistance to tearing. While previously described gels, such as KP-12, meet some of these requirements, they also tend to exhibit a high degree a tack. Tackiness is particularly a problem in the case of gel rollers in trocar seals. The gel trocar seal in one aspect uses rotational movement of two opposed gel rollers such that the gel rollers contact each other and freely roll in response to inserted instrumentation. The gel rollers also roll relative to the trocar housing. A high degree of tackiness may inhibit the rotational movement of the rollers.

In hand access devices, high tackiness may inhibit passage of instruments or the surgeon's hand through the device, requiring the use of lubricants such as petrolatum on the gloved hand or instrument. A hand-access device pre-coated with a lubricant such as oil or petrolatum is messy and difficult to handle, and requiring the surgeon to apply a lubricant either onto his or her gloved hand, the access device and/or the medical instruments to be inserted therethrough requires additional time and additional materials in the operating room.

What is needed, therefore, are composite gel materials that exhibit low durometer, high tear strength, high elongation, high compliance, resistance to compression, and a non-tack surface. Alternatively, what is needed are coatings for gel materials that are quickly and easily activated to reduce tack and/or increase lubricity of the gel materials and to reduce frictional forces between mating gel material components and/or between gel material components and/or non-gel material components.

SUMMARY

In one aspect, the invention is directed to a surgical device having at least one component formed from a gel material having a non-tack surface, the gel material comprising a copolymer, a mineral oil and a low viscosity silicone oil.

In one aspect, the copolymer comprises a styrene ethylene butylene styrene (SEBS) copolymer. In another aspect, the copolymer comprises a styrene ethylene ethylene propylene styrene copolymer (SEEPS) copolymer.

In one aspect of the invention, the silicone oil has a viscosity from about 1 to about 10 centistokes. In another aspect, the silicone oil has a viscosity of about 5 centistokes.

In one aspect of the invention, the gel material is opaque. In another aspect of the present invention, the gel material is transparent.

In one aspect, the invention is directed to a surgical device having at least one component formed from a gel material having a non-tack surface, the gel material comprising a copolymer and a blend of a high viscosity mineral oil and a low viscosity mineral oil. In one aspect, the copolymer comprises a styrene ethylene butylene styrene (SEBS) copolymer.

In one aspect, the low viscosity mineral oil has a viscosity from about 1 to about is 16 centistokes. In another aspect, the high viscosity oil has a viscosity from about 25 to about 125 centistokes.

In one aspect, the invention is directed to a surgical device having at least one component formed from a gel material having a non-tack surface, the gel material comprising a copolymer and a synthetic oil. In one aspect, the copolymer comprises a styrene ethylene butylene styrene (SEBS) copolymer. In another aspect, the copolymer comprises a styrene ethylene ethylene propylene styrene copolymer (SEEPS) copolymer.

In one aspect of the invention, the synthetic oil comprises a polyalfaolefin (PAO) oil, a polyolester (POE) oil, a polybutene oil, or mixtures thereof.

In one aspect of the invention, the surgical device is a trocar. In another aspect of the invention, the surgical device is a hand access device.

In one aspect of the invention, a lubricious agent is coated on at least one surface of the gel material. In one aspect, the agent is a dry film and may comprise an anti-fogging agent, a hydrophilic coating, a soap, or a mixture thereof. The lubricious agent may be activated before use by the application of water or saline.

In another aspect, the invention is directed to a non-tacky gel useful as a component of a surgical device, the gel comprising a copolymer, a mineral oil and a low viscosity silicone oil. In one aspect, the copolymer comprises a styrene ethylene butylene styrene (SEBS) copolymer. In another aspect, the copolymer comprises a styrene ethylene ethylene propylene styrene copolymer (SEEPS) copolymer. In another aspect of the invention, the silicone oil has a viscosity from about 1 to about 10 centistokes.

In another aspect, the invention is directed to a non-tacky gel useful as a component of a surgical device, the gel comprising a copolymer and a blend of at least one high viscosity mineral oil and at least one low viscosity mineral oil. In one aspect, the copolymer comprises a styrene ethylene butylene styrene (SEBS) copolymer.

In another aspect, the present invention is directed to a non-tacky gel useful as a component of a surgical device, the gel comprising a copolymer and a synthetic oil. In one aspect, the copolymer comprises a styrene ethylene butylene styrene (SEBS) copolymer; in another aspect, the copolymer comprises a styrene ethylene ethylene propylene styrene copolymer (SEEPS) copolymer.

In one aspect of the invention, the synthetic oil comprises a polyalfaolefin (PAO) oil, a polyolester (POE) oil, a polybutene oil, or mixtures thereof.

In one aspect, the invention is directed to a method for assembling a medical device having a housing and at least one component comprising a gel material disposed within the housing, the method comprising the steps of freezing the gel component, inserting the frozen gel component into the housing, and allowing the gel component to return to room temperature.

In another aspect, the invention is directed to a method for increasing the lubricity of a trocar seal, the method comprising the step of applying an anti-fogging solution to the seal, and to trocar seals having a coating of an anti-fogging solution.

DETAILED DESCRIPTION

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the structures and/or methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The present invention is directed to gel materials, and surgical devices containing gel materials, having reduced tackiness while retaining low durometer, high tear strength, high elongation, high compliance, and resistance to compression.

These properties of the prior art materials are far exceeded by the properties associated with the present invention which in some respects provide a full magnitude of advantage. In fact, the difference between the materials of the prior art and the materials of the present invention are sufficiently substantial, that it is perhaps misleading to refer to the present material as merely a gel. According, the material of the present invention, having properties including an ultimate elongation greater than about 1000 percent and a durometer less than about 5Shore A, will be referred to herein as an "ultragel."

In a preferred embodiment of the present invention, the ultragel includes KRATON and mineral oil and provides a sealing material with the following properties: an ultimate elongation exceeding about 1500 percent, and a durometer of less than about 200 Bloom. The durometer in this case is considerably lower than that of the prior art materials. In fact, the durometer of the present material is so soft it cannot even be measured on the Shore A scale.

The resulting elongation and durometer of the present material facilitates its use with as an access valve which is capable of forming seals with a full range of instrument sizes, but is also capable of functioning as a zero seal. Whereas access devices of the prior art may have required as many as six separate seals in order to accommodate a full range of instrument sizes, access devices can now be made with only a single valve formed of the ultragel material.

Surgical devices incorporating gel materials have been previously described. Two examples, illustrative of such devices, are shown in FIGS. 1 and 2.

Figure 1A:
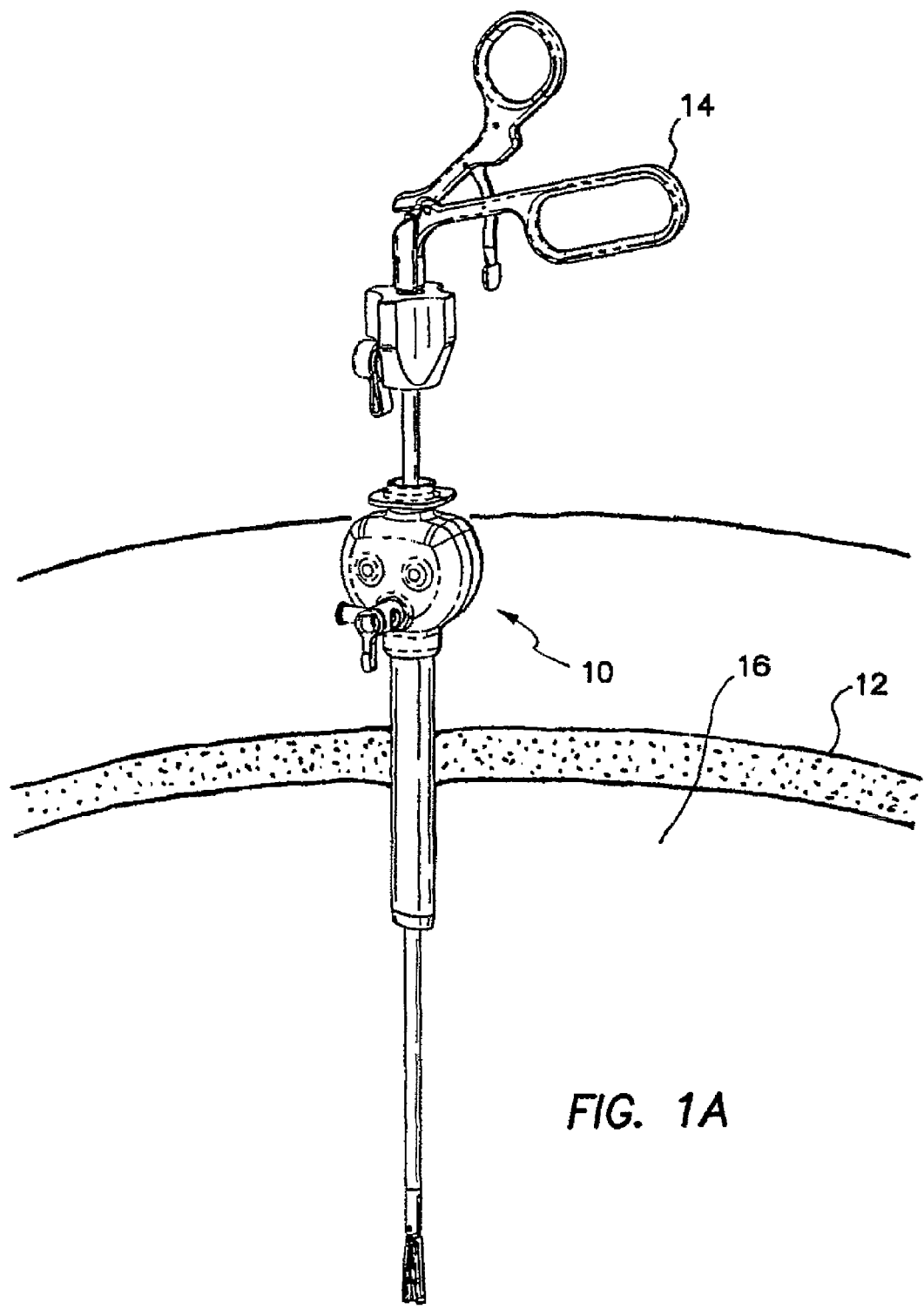
FIG. 1 is a drawing showing an example of a trocar having a seal housing containing gel rollers.
Figure 1B:
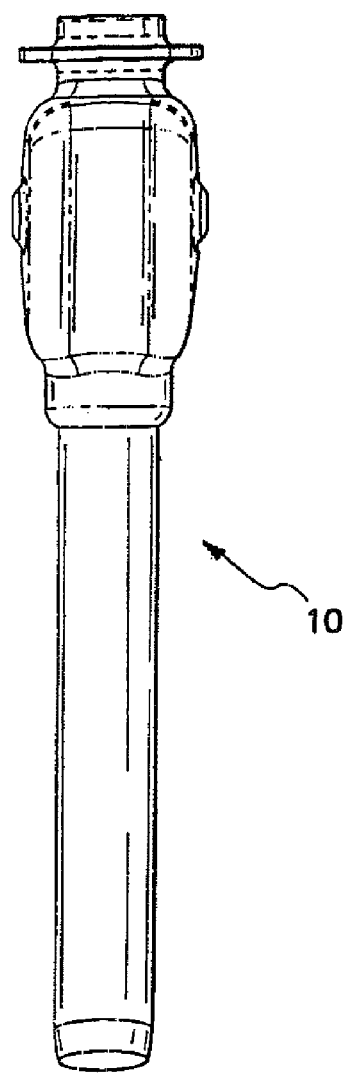
Figure 1C:
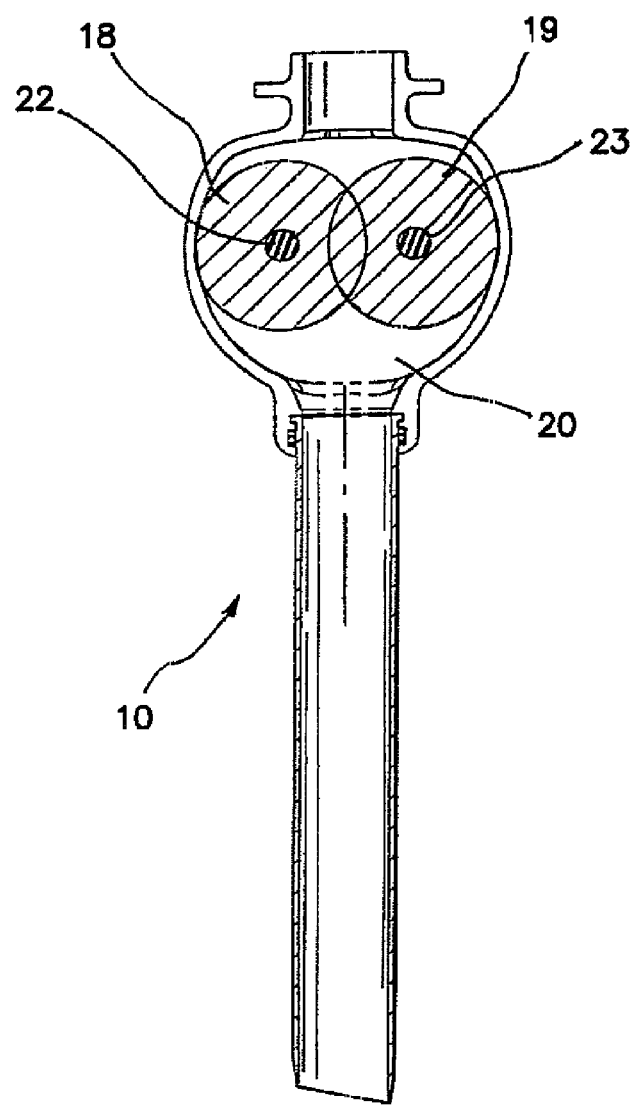

FIG. 1 shows a trocar having a seal housing containing two opposed rollers comprising a gel material. FIG. 1(a) shows the trocar disposed across the body wall (12) of a patient, with a medical instrument, in this case, a laparoscopic grasper 14, inserted through the trocar into the body cavity 16 of the patient. FIGS. 1(b) and (c) show a side and front view of a trocar, respectively, the front view (c) cut-away to show a pair of gel rollers 18, 19 disposed within the seal housing 20 of the trocar. The gel rollers 18, 19 rotate around a pair of axles 22, 23.

Figure 2A:
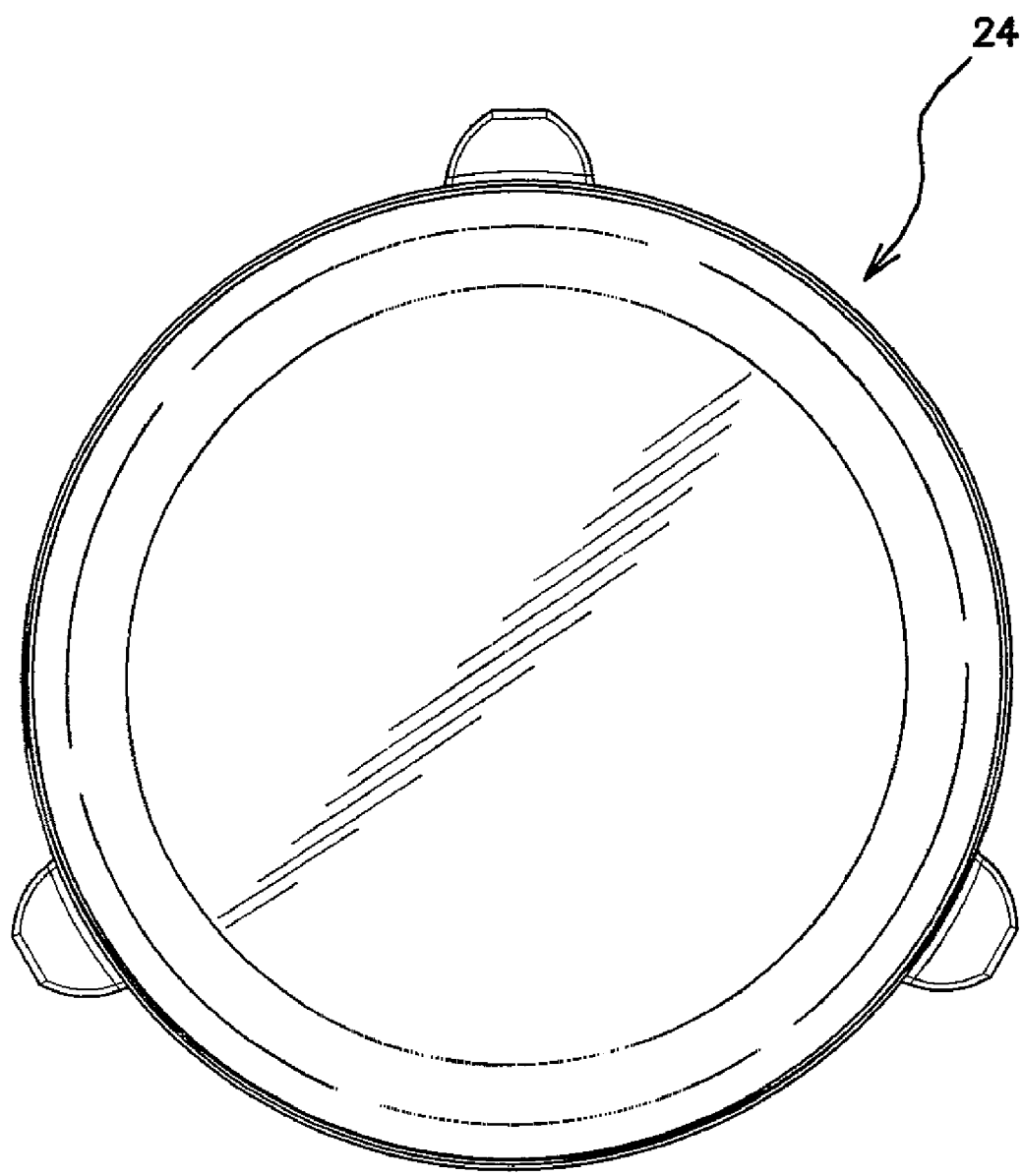
FIG. 2 is a drawing showing examples of hand access devices having a gel component.
Figure 2B:
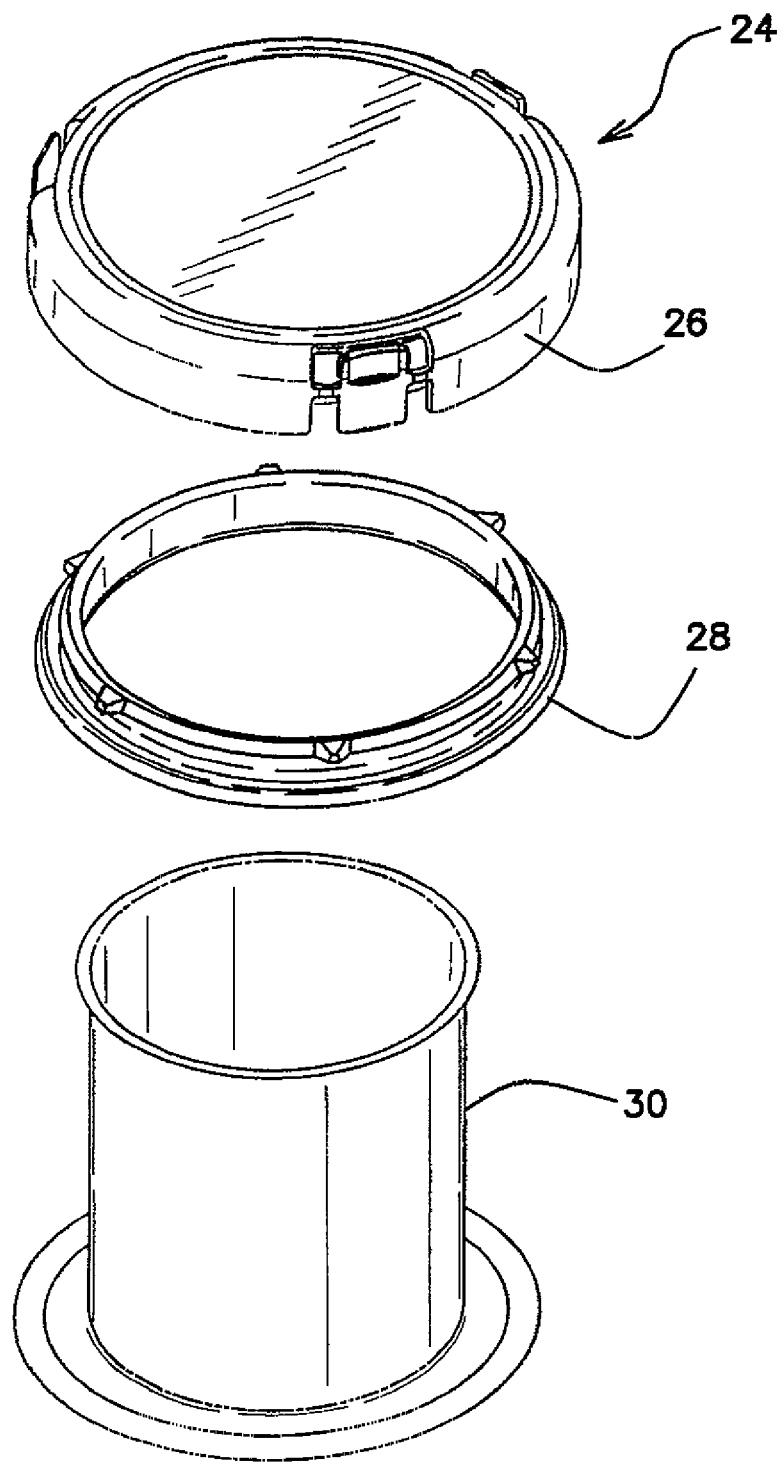
Figure 2C:
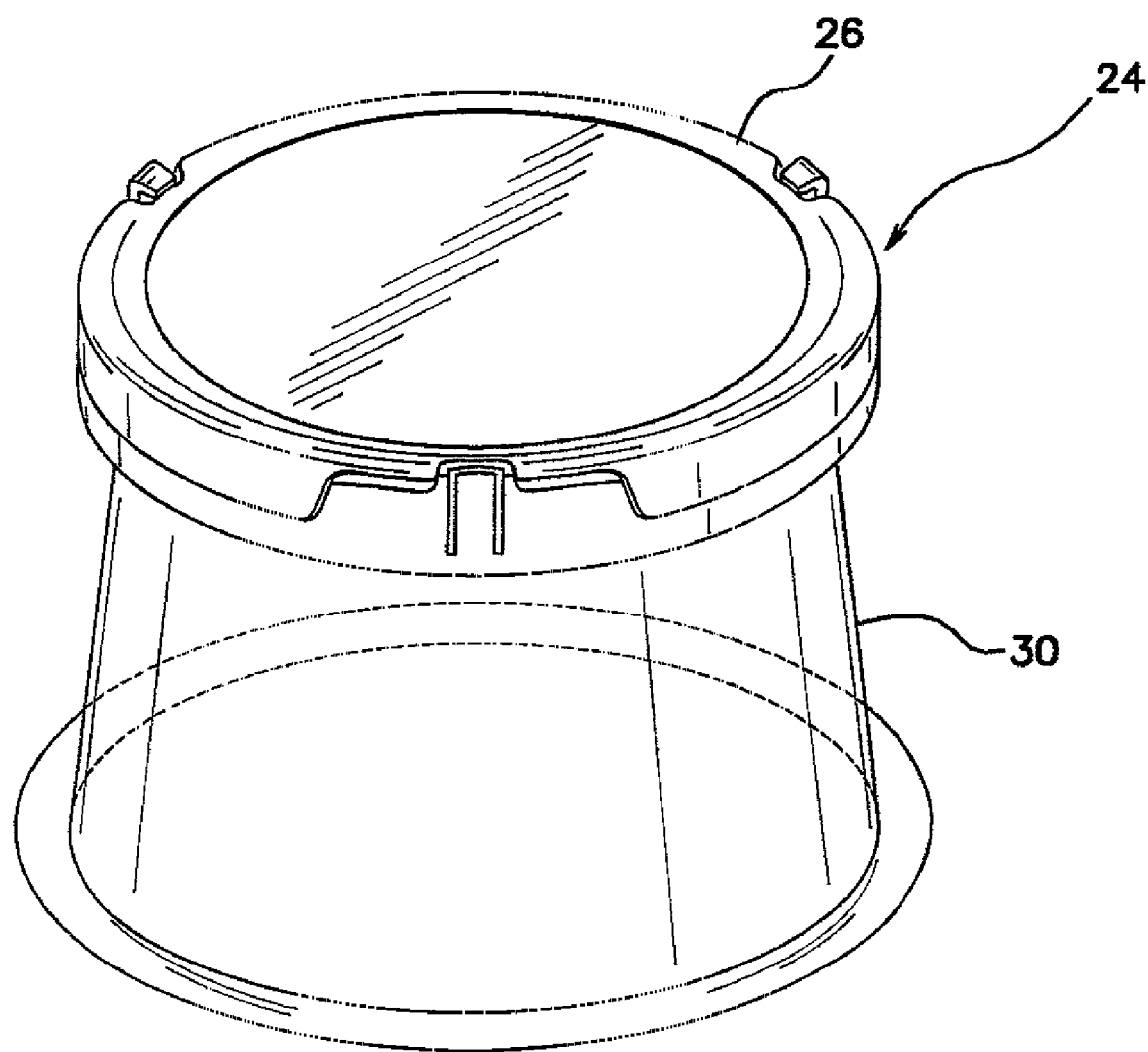

FIGS. 2(a)-2(c) show examples of hand access devices having a gel cap. FIG. 2(a) shows a top view of a gel cap 24 of a hand access device. FIG. 2(b) shows an exploded view of a hand access device, including a gel cap 24 contained in an annular housing 26, ring 28 and retractor sleeve 30. FIG. 2(c) shows a perspective view of an assembled hand access device having a gel cap.

Gel coatings. In one aspect, the present invention is directed to gel materials and surgical devices containing gel materials, wherein the gel materials have been provided with a coating to produce a lubricious surface and to reduce tackiness.

The gel material in one aspect can be coated with a lubricious solution, such as a solution containing an anti-fogging agent, a hydrophilic agent, soap, or a silicone oil/water emulsion like ARMOR-ALL®, for example, and allowed to dry, leaving a film of the lubricious agent on the gel. The lubricious agent can be activated just before use with the application of a small amount of a solvent such as water, saline, or additional lubricious solution to produce a lubricious surface. The solvent is preferably sprayed on the gel material but may be brushed, dropped, poured or otherwise applied to provide adequate coverage of the gel material and activation of the lubricious agent.

Surgical devices containing gel materials coated with a dry film of a lubricious agent can be more easily packaged and stored than those containing wet or oily coatings. Similarly, hand access devices containing gel materials coated with a dry film of a lubricious agent can be more easily manipulated and inserted into the patient by the surgeon prior to activating the lubricious coating.

In one aspect, the lubricious agent is an anti-fogging agent. Preferably, the gel material is coated with the anti-fogging solution and allowed to dry leaving a film of the antifogging agent on the gel. The anti-fogging agent can be activated just before use with the application of a small amount of water, saline, or the anti-fogging solution to produce a lubricious surface, as described above. Alternatively, the anti-fogging solution can be applied to the gel just prior to use to produce a lubricious gel surface.

Using an anti-fogging agent to produce a lubricious gel surface may have other benefits beyond reducing tackiness of the gel material. For example, when a gel material in a trocar seal housing is treated with an anti-fogging agent, which is then activated prior to inserting a laparoscope, the anti-fogging solution also serves to coat the lens of a laparoscope as the laparoscope is passed through the gel. The anti-fogging agent acts as a surfactant to prevent condensation droplets from beading up on the lens of the laparoscope thereby enhancing the visualization through the laparoscope. Condensation can develop on the lens of a laparoscope when the laparoscope is moved from a cool dry environment such as an operating room to a warm moist environment such as the peritoneal cavity of a patient. During laparoscopic surgery, if condensation occurs on the lens of the laparoscope, the visibility of the operative field for the surgeon becomes obscured and the laparoscope is removed from the trocar and the lens of the laparoscope manually wiped clean. This can occur numerous times during a laparoscopic procedure which can disrupt the procedure and increase the time utilized to complete the procedure.

A medical grade anti-fogging solution suitable for practice of the present invention comprises a mixture of 1% by weight docusate sodium or dioctyl sulfosuccinate, and 99% by weight distilled water. A commercially available medical grade anti-fogging solution is the TYCO® FRED®-Lite anti-fog solution.

To create a dry film of the anti-fogging agent that can later be activated with saline, a higher concentration solution, in the range of about 2% to about 10% by weight docusate sodium, can be utilized. When this higher concentration of the anti-fogging solution is applied to the gel and allowed to dry as a film, saline can be used to activate the anti-fogging agent, resulting in an effective anti-fogging and lubricious solution present on the surface of the gel.

Various other applications of the anti-fogging solution are also available. For example, the anti-fogging solution can be used in other trocar seals which utilize septum seals and duckbill valve or flapper valve type seals made from polyisoprene, silicone, or other elastomeric materials. The anti-fogging agent can be applied in the form of a dry film within the trocar seals and activated prior to use with the application of saline or the anti-fogging solution. In one aspect, the anti-fogging solution can be used as a wet lubricant within the trocar seals. For example, if a shielded or multi-layered type of septum seal is utilized, the anti-fogging solution can be applied between each of the individual layers to act as an instrument lubricant, a lubricant between the layers of the septum seal, and as an anti-fogging agent for an inserted laparoscope. A multi-layered septum seal can also use lubrication between the layers in order for the septum seal to expand and conform around inserted instruments and to maintain a seal. The lubrication typically used is a silicone based lubricant which can adhere to and/or smear the lens of a laparoscope as it is inserted through a multi-layered septum seal. This can result in decreased visibility through the laparoscope. Use of the anti-fogging solution on such septum seals obviates the laparoscope visibility issues.

In addition to anti-fogging agents, hydrophilic agents may be used to coat gel materials to produce a tack-free surface on the gel. The hydrophilic coating is activated with the application of a small amount of water or saline. This results in a gel with a lubricious surface. The hydrophilic coating in one aspect is sprayed onto the gel and/or the gel can be dipped into a hydrophilic solution to apply the coating. Hydrophilic agents suitable for practice of the present invention include polymers such as polyethylene oxide (PEO), polyethylene glycol (PEG), polyvinyl pyrrolidone (PVP), polyurethane (PU), and mixtures thereof.

In another aspect, the gel material may be coated with a cleanser, such as soap, and allowed to dry leaving a film, e.g., a soap film, on the gel. The soap is activated with the application of a small amount of water, saline, or a soap solution to produce a lubricious surface. In one aspect, a soap solution is applied to the gel prior to use to produce a lubricious gel surface.

In still another aspect, the gel material is lubricated with a silicone oil and water emulsion, such as that sold under the trade name ARMOR-ALL®, to produce a lubricious gel surface.

In addition to providing lubricious coatings to gel materials, it has been found that exposing the gel material to different temperature ranges may affect tackiness. For example, freezing the gel material is effective to render the surface of the gel temporarily tack-free. In one aspect of the present invention, the gel material is frozen to facilitate handling of tacky gel materials prior to the application of coatings or lubricants. Also, for example, if a component comprised of a gel material is to be assembled into a housing or the like, and the design of that housing is such that it is difficult to insert the gel component, due to a tight fit, for example, the gel component can be deformed or otherwise manipulated and frozen into a state facilitating its insertion. The frozen, deformed gel component can then be optionally coated and easily installed into the housing, regaining its original shape after warming to room temperature.

In addition to providing coatings to reduce the tackiness of gel materials, another aspect of the present invention is directed to new gel compositions, in which the gel material is modified to reduce tackiness. Thus, in various aspects in accordance with the present invention, solutions to produce a tack-free gel material by modifying the known KP-12 gel formulation by including additives and/or by changing one or more of its constituent components are provided. Examples of such solutions are as follows.

Low viscosity silicone oil additives. In one aspect of the present invention, the KP-12 gel material is modified by the inclusion of a low viscosity silicone oil as an additive. The effect of adding the silicone oil is to reduce the surface tackiness of the gel material, although the result is dependent on the viscosity of the silicone oil.

Gel materials created with low viscosity mineral oils of less than about 50 centistokes are generally tack-free. These tack-free gels, however, may not exhibit a desirable resistance to compression set in comparison to gels created with higher viscosity mineral oils. By adding low viscosity silicone oil to the KP-12 gel, the surface tackiness of the gel is reduced while the compression set properties of the original gel material is maintained. The addition of a low viscosity silicone oil to the existing KP-12 gel formulation resulted in a gel which was largely tack-free and retained the compression set properties of the original KP-12 gel. Examples of such gel formulations with silicone oil in accordance with various aspects of the present invention are as follows (all parts are by weight):

Example 1

8 parts DRAKEOL® 35 mineral oil (viscosity of 68 centistokes), 1 part CLEARCO® 5 silicone oil (viscosity of 5 centistokes), and 1 part KRATON® G-1651 copolymer.

Example 2

7.5 parts of DRAKEOL® 35 mineral oil (viscosity of 68 centistokes), 1.5 parts CLEARCO® 1 silicone oil (viscosity of 1 centistokes), and 1 part KRATON® G-1651 copolymer.

Example 3

7.5 parts DRAKEOL® 35 mineral oil (viscosity of 68 centistokes), 1.5 parts CLEARCO® 5 silicone oil (viscosity of 5 centistokes), and 1 part KRATON® G-1651 copolymer.

Example 4

72 parts of DRAKEOL® 600 mineral oil (viscosity of 106 centistokes), 2 parts of CLEARCO® 5 silicone oil (viscosity of 5 centistokes), and 1 part KRATON® G-1651 copolymer.

Example 5

7.2 parts DRAKEOL® 35 mineral oil (viscosity of 68 centistokes), 1.8 parts CLEARCO® 5 silicone oil (viscosity of 5 centistokes), and 1 part KRATON® G-1651 copolymer.

Example 6

7.2 parts DRAKEOL® 35 mineral oil (viscosity of 68 centistokes), 1.7 parts CLEARCO® 5 silicone oil (viscosity of 5 centistokes), and 1.1 parts KRATON® G-1651 copolymer.

Example 7

7 parts DRAKEOL® 35 mineral oil (viscosity of 68 centistokes), 2 parts CLEARCO® 1 silicone oil (viscosity of 1 centistokes), and 1 part KRATON® G-1651 copolymer.

Example 8

7 parts DRAKEOL® 35 mineral oil (viscosity of 68 centistokes), 2 parts CLEARCO® 5 silicone oil (viscosity of 5 centistokes), and 1 part KRATON®G-1651 copolymer.

Example 9

6.9 parts DRAKEOL® 35 mineral oil (viscosity of 68 centistokes), 2 parts CLEARCO® 5 silicone oil (viscosity of 5 centistokes), and 1.1 parts KRATON® G-1651 copolymer.

Example 10

6.8 parts DRAKEOL® 35 mineral oil (viscosity of 68 centistokes), 21 parts CLEARCO® 5 silicone oil (viscosity of 5 centistokes), and 1.1 parts KRATON® G-1651 copolymer.

Example 11

6.5 parts DRAKEOL® 35 mineral oil (viscosity of 68 centistokes), 2.5 parts CLEARCO® 5 silicone oil (viscosity of 5 centistokes), and 1 part KRATON® G-1651 copolymer.

Example 12

6 parts DRAKEOL® 35 mineral oil (viscosity of 68 centistokes), 3 parts CLEARCO® 5 silicone oil (viscosity of 5 centistokes), and 1 part KRATON® G-1651 copolymer.

The examples provided should be considered in all respects as illustrative and not restrictive.

In testing the above formulations, gels with the low-viscosity silicone oil additive exhibited a temperature-dependent change in optical clarity. Gels having 1.8 parts or more of CLEARCO® 5 silicone oil as an additive are opaque at room temperature and become transparent at slightly higher temperatures. In a specific example, a gel with 1.8 parts of the CLEARCO® 5 silicone oil is opaque at room temperature and becomes transparent when heated to about 100° F. The amount of silicone oil present in the gel material can determine the temperature at which the transition from opaque to transparent occurs. For example, a gel with 1.5 parts of the CLEARCO® 5 silicone oil is transparent at room temperature, but becomes opaque when placed into a freezer for about 10 seconds.

SEEPS-based gels. In another aspect of the present invention, the copolymer component of the KP-12 gel is changed from a SEBS (styrene ethylene butylene styrene) copolymer (specifically, a KRATON® SEBS) to a SEEPS (styrene ethylene ethylene propylene styrene) copolymer (specifically, KURARAY™ SEPTON® SEEPS), and a low-viscosity silicone oil is added to produce a high-strength tack-free gel. In various aspects, such gels have lower surface tackiness in comparison to KP-12 gel and maintain the resistance to compression set similar to that of KP-12 gel material. Examples of such gel formulations with the SEEPS copolymer and the silicone oils in accordance with various aspects of the present invention are as follows (all parts are by weight):

Example 13

7.8 parts DRAKEOL® 35 mineral oil (viscosity of 68 centistokes), 1.5 parts CLEARCO® 5 silicone oil (viscosity of 5 centistokes), and 0.7 parts KURARAY™ SEPTON® 4099 copolymer.

Example 14

7.2 parts DRAKEOL® 35 mineral oil (viscosity of 68 centistokes), 1.7 parts CLEARCO® 5 silicone oil (viscosity of 5 centistokes), and 1.1 parts KURARAY™ SEPTON®4044 copolymer.

Example 15

7.2 parts DRAKEOL® 35 mineral oil (viscosity of 68 centistokes), 1.8 parts CLEARCO® 5 silicone oil (viscosity of 5 centistokes), and 1 part KURARAY™ SEPTON® 4033 copolymer.

Example 16

7.1 parts DRAKEOL® 35 mineral oil (viscosity of 68 centistokes), 2 parts CLEARCO® 5 silicone oil (viscosity of 5 centistokes), and 0.9 parts KURARAY™ SEPTON® 4099 copolymer.

Example 17

7 parts DRAKEOL® 600 mineral oil (viscosity of 106 centistokes), 2 parts CLEARCO® 5 silicone oil (viscosity of 5 centistokes), and 1 part KURARAY™ SEPTON® 4077 copolymer.

Example 18

7 parts DRAKEOL® 600 mineral oil (viscosity of 106 centistokes), 2 parts CLEARCO® 5 silicone oil (viscosity of 5 centistokes), and 1 part KURARAY™ SEPTON® 4055 copolymer.

Example 19

7 parts DRAKEOL® 35 mineral oil (viscosity of 68 centistokes), 2 parts CLEARCO® 5 silicone oil (viscosity of 5 centistokes), and 1 part KURARAY™ SEPTON®4077 copolymer.

Example 20

7 parts DRAKEOL® 35 mineral oil (viscosity of 68 centistokes), 2 parts CLEARCO® 5 silicone oil (viscosity of 5 centistokes), and 1 part KURARAY™ SEPTON® 4055 copolymer.

The examples provided should be considered in all respects as illustrative and not restrictive.

Gels with blended oils of mixed viscosities. In one aspect, the gel material is modified such that mineral oils with different viscosities are blended with a SEBS copolymer to produce a gel with resistance to compression set and with a tack-free surface. As mentioned above, gel materials with a high viscosity mineral oil have a resistance to compression set and a very tacky outer surface. In one aspect, low viscosity mineral oil(s) are blended with high viscosity mineral oil(s) to produce a tack-free gel with resistance to compression set. Generally, however, in various aspects of the present invention, gels with the blended oils provide decreased tackiness, but also provide a reduction in resistance to compression set. Examples of such gel formulations with blended mineral oils in accordance with various aspects of the present invention are as follows (all parts are by weight):

Example 21

8 parts DRAKEOL® 600 (viscosity of 106 centistokes), 1 part DRAKEOL® 5 (viscosity of 8 centistokes), 1 part KRATON® G-1651 copolymer

Example 22

8 parts DRAKEOL® 5 (viscosity of 8 centistokes), 1 part DRAKEOL® 600 (viscosity of 106 centistokes), 1 part KRATON® G-1651 copolymer.

Example 23

7.5 parts DRAKEOL® 5 (viscosity of 8 centistokes), 1.5 parts DRAKEOL® 35 (viscosity of 68 centistokes), 1 part KRATON® G-1651 copolymer.

Example 24

7.5 parts DRAKEOL® 5 (viscosity of 8 centistokes), 1.5 parts DRAKEOL® 15 (viscosity of 29 centistokes), 1 part KRATON® G-1651 copolymer.

Example 25

7 parts DRAKEOL® 5 (viscosity of 8 centistokes), 1.5 parts DRAKEOL® 15 (viscosity of 29 centistokes), 1.5 parts KRATON® G-1651 copolymer.

Example 26

7 parts DRAKEOL® 5 (viscosity of 8 centistokes), 1 part DRAKEOL® 35 (viscosity of 68 centistokes), 2 parts KRATON® G-1651 copolymer.

Example 27

4.8 parts DRAKEOL® 35 (viscosity of 68 centistokes), 4.2 parts DRAKEOL® 5 (viscosity of 8 centistokes), 1 part KRATON® G-1651 copolymer.

Example 28

4.5 parts DRAKEOL® 5 (viscosity of 8 centistokes), 4.5 parts DRAKEOL® 15 (viscosity of 29 centistokes), 1 part KRATON® G-1651 copolymer.

Example 29

4.5 parts DRAKEOL® 5 (viscosity of 8 centistokes), 4.5 parts DRAKEOL® 35 (viscosity of 68 centistokes), 1 part KRATON® G-1651 copolymer.

The examples provided should be considered in all respects as illustrative and not restrictive.

Gels made with synthetic oils. In another aspect of the present invention, the gel material is made with a synthetic oil in place of a mineral oil. In some examples, the SEBS copolymer component is also replaced with an SEEPS copolymer. In some formulations, for example, polyalfaolefin (PAO) oils, polyolester (POE) oils, and polybutene oils are used as direct replacements and/or as supplements for the mineral oil.

Gel materials with the DURASYN® 162 synthetic PAO oil have a reduced tackiness in comparison to the KP-12 gel but demonstrate a reduced or low resistance 5 to compression set. Gel materials with the DURASYN® 164 synthetic PAO oil are largely equivalent to KP-12 gel. Gel materials made with a SUMMIT® Ultima POE synthetic oil provide low strength and low resistance to compression set. Gel materials with AMOCO® INDOPOL® polybutene oil provide high resistance to compression set but can be largely oily on the surface. Examples of gel formulations with synthetic oils in accordance with various aspects of the present invention are as follows (all parts are by weight):

Example 30

9 parts DURASYN® 162 synthetic oil (viscosity of 5.5 centistokes), and 1 part KRATON® G-1651 copolymer.

Example 31

9 parts DURASYN® 164 synthetic oil (viscosity of 17 centistokes), 15 and 1 part KRATON® G-1651 copolymer.

Example 32

9 parts INDOPOL® L-14 synthetic oil (viscosity of 46 centistokes), 1 part KURARAY™ SEPTON® 4077 copolymer.

Example 33

9 parts INDOPOL® L-14 synthetic oil (viscosity of 46 centistokes), 1 part KRATON® G-1651 copolymer.

Example 34

9 parts Ultima 150 synthetic oil (viscosity of 46 centistokes), 1 part KRATON® G-1651 copolymer.

Example 35

4.5 parts DRAKEOL® 600 (viscosity of 106 centistokes), 4.5 parts Ultima 150 synthetic oil (viscosity of 46 centistokes), 1 part KRATON® G-1651 copolymer.

Example 36

4.5 parts DRAKEOL® 5 (viscosity of 8 centistokes), 4.5 parts Ultima 150 synthetic oil (viscosity of 46 centistokes), 1 part KRATON® G-1651 copolymer.

The examples provided should be considered in all respects as illustrative and not restrictive.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive. Also, all the examples provided throughout the entire description should be considered in all respects as illustrative and not restrictive. The scope of the invention is, therefore, indicated by the following claims rather than by the foregoing description. All changes, modifications, and variations coming within the meaning and range of equivalency of the claims are to be considered within their scope.

The invention claimed is:

1. A surgical device comprising a trocar with a seal housing at the proximal end and at least one roller disposed inside the seal housing and configured to seal and roll relative to the seal housing; the roller being formed from a gel material having a non-tack surface, the gel material comprising a copolymer, a mineral oil and a low viscosity silicone oil wherein the gel material has an elongation of greater than about 1000%.

2. The surgical device of claim 1, wherein the copolymer comprises a styrene ethylene butylene styrene (SEBS) copolymer.

3. The surgical device of claim 1, wherein the silicone oil has a viscosity from about 1 to about 50 centistokes.

4. The surgical device of claim 3, wherein the silicone oil has a viscosity of about 5 centistokes.

5. The surgical device of claim 3 wherein the gel material comprises by weight at least about 6:1 mineral oil to copolymer, and at least about 1:1 low viscosity silicone oil to copolymer.

6. The surgical device of claim 1, wherein the gel material is opaque.

7. The surgical device of claim 1, wherein the gel material is transparent.

8. The surgical device of claim 1, wherein the device includes two opposed rollers disposed inside the trocar housing and configured to seal and roll relative to the trocar housing and configured to receive an instrument inserted between the two rollers and into the trocar.

9. The surgical device of claim 1, wherein the device comprises a hand access device.

10. The surgical device of claim 1, wherein the gel material further comprises a lubricious agent deposited on at least one surface of the gel material.

11. The surgical device of claim 10, wherein the lubricious agent comprises a dry film.

12. The surgical device of claim 10, wherein the lubricious agent comprises an anti-fogging agent.

13. The surgical device of claim 12 wherein the roller is configured to coat a laparoscope inserted into the trocar with the anti-fogging agent.

14. The surgical device of claim 10, wherein the lubricious agent comprises a hydrophilic coating.

15. The surgical device of claim 10, wherein the lubricious agent comprises a soap.

16. The surgical device of claim 1, wherein the copolymer comprises a styrene ethylene ethylene propylene styrene copolymer (SEEPS) copolymer.

17. The surgical device of claim 1, wherein the gel material comprises by weight at least about 6:1 mineral oil to copolymer.

18. The surgical device of claim 1, wherein the gel material comprises by weight at least about 1:1 low viscosity silicone oil to copolymer.

19. The surgical device of claim 1, wherein the gel material comprises by weight at least about 6:1 mineral oil to copolymer, and at least about 1:1 low viscosity silicone oil to copolymer.

20. The surgical device of claim 1 wherein the silicone oil has a viscosity from about 1 to about 15 centistokes.

21. A surgical device comprising:
a trocar including a seal housing at a proximal end of the trocar; and
a non-tacky gel component, the component being disposed in the seal housing at the proximal end of the trocar; the component being configured to move relative to the seal housing to create a seal inside the trocar; the gel comprising a copolymer, a mineral oil and a low viscosity silicone oil, wherein the gel material has an elongation of greater than about 1000%.

22. The surgical device of claim 21, wherein the copolymer comprises a styrene ethylene butylene styrene (SEBS) copolymer.

23. The surgical device of claim 21, wherein the copolymer comprises a styrene ethylene ethylene propylene styrene copolymer (SEEPS) copolymer.

24. The gel of claim 21, wherein the silicone oil has a viscosity from about 1 to about 50 centistokes.

25. The surgical device of claim 21, comprising by weight at least about 6:1 mineral oil to copolymer.

26. The surgical device of claim 21, comprising by weight at least about 1:1 low viscosity silicone oil to copolymer.

27. The surgical device of claim 21, comprising by weight at least about 6:1 mineral oil to copolymer, and at least about 1:1 low viscosity silicone oil to copolymer.

28. The surgical device of claim 21 wherein the silicone oil is incorporated in the gel to create a non-tack surface.

29. The surgical device of claim 28 wherein the silicone oil has a viscosity from about 1 to about 50 centistokes.

30. The surgical device of claim 21 wherein the gel material has a resistance to compression set.

\* \* \* \* \*